US 9,140,661 B2

(12) United States Patent
Marcotte et al.

(10) Patent No.: US 9,140,661 B2
(45) Date of Patent: Sep. 22, 2015

(54) ELECTRODE CONFIGURATION FOR LIMCA

(71) Applicant: NOVELIS INC., Atlanta, GA (US)

(72) Inventors: Jacques Marcotte, Ste-Brigitte-de-Laval (CA); Yuhil Slusarenko, Ste-Foy (CA)

(73) Assignee: Novelis Inc., Atlanta, GA (US)

( * ) Notice: Subject to any disclaimer, the term of this patent is extended or adjusted under 35 U.S.C. 154(b) by 0 days.

(21) Appl. No.: 14/501,614

(22) Filed: Sep. 30, 2014

(65) Prior Publication Data
US 2015/0021206 A1     Jan. 22, 2015

Related U.S. Application Data

(63) Continuation of application No. 12/290,257, filed on Oct. 29, 2008, now Pat. No. 8,928,306, which is a continuation of application No. 11/067,768, filed on Feb. 28, 2005, now Pat. No. 7,459,896.

(60) Provisional application No. 60/550,998, filed on Mar. 4, 2004.

(51) Int. Cl.
| G01N 27/403 | (2006.01) |
| G01N 33/20 | (2006.01) |
| G01N 15/02 | (2006.01) |

(52) U.S. Cl.
CPC .............. *G01N 27/403* (2013.01); *G01N 15/02* (2013.01); *G01N 33/206* (2013.01)

(58) Field of Classification Search
USPC ........................................................ 324/71.4
See application file for complete search history.

(56) References Cited

U.S. PATENT DOCUMENTS

| 3,259,891 A | 7/1966 | Coulter et al. |
| 3,340,470 A | 9/1967 | Coulter, Jr. |
| 3,340,471 A | 9/1967 | Coulter, Jr. |

(Continued)

FOREIGN PATENT DOCUMENTS

| AU | 2005218076 B2 | 11/2010 |
| AU | 2010235916 B2 | 6/2012 |

(Continued)

OTHER PUBLICATIONS

European Patent Application No. EP 05 714 516.1, Office Action mailed Sep. 29, 2014, 7 pages.

(Continued)

*Primary Examiner* — Thomas F Valone
(74) *Attorney, Agent, or Firm* — Kilpatrick Townsend & Stockton, LLP

(57) ABSTRACT

Disclosed is a method and apparatus for reducing electromagnetic noise pick up in a Liquid Metal Cleanliness Analyzer (LiMCA), used to detect and measure particles in molten metal. A first electrode inserted in the molten metal is electrically insulated from second and third electrodes, also inserted in the molten metal. Molten metal and particles pass between the first electrode and the second and third electrodes through a passage in the electrical insulation. The second and third electrodes have a configuration with respect to the first electrode sufficient to establish symmetrical current loops between the first electrode and the second and third electrodes when a current is supplied to the second and third electrodes. The current is supplied from an ultra-capacitor. Electromagnetic noise in the symmetrical current loops is detected and is added in opposition to reduce the amplitude of the electromagnetic noise.

20 Claims, 1 Drawing Sheet

(56) References Cited

U.S. PATENT DOCUMENTS

| | | | |
|---|---|---|---|
| 3,502,974 | A | 3/1970 | Coulter et al. |
| 3,529,239 | A | 9/1970 | Valley et al. |
| 3,944,917 | A | 3/1976 | Hogg et al. |
| 3,987,391 | A | 10/1976 | Hogg |
| 4,161,690 | A | 7/1979 | Feier |
| 4,435,681 | A | 3/1984 | Masuda et al. |
| 4,527,114 | A | 7/1985 | Coulter |
| 4,555,662 | A | 11/1985 | Doutre et al. |
| 4,600,880 | A | 7/1986 | Doutre et al. |
| 4,963,715 | A | 10/1990 | Tuttle |
| 5,025,220 | A | 6/1991 | Colvin et al. |
| 5,039,935 | A | 8/1991 | Hachey et al. |
| 5,130,639 | A | 7/1992 | Hachey |
| 5,241,262 | A | 8/1993 | Guthrie et al. |
| 5,343,016 | A | 8/1994 | Davis et al. |
| 5,789,910 | A | 8/1998 | Guthrie |
| 5,834,928 | A | 11/1998 | Doutre |
| 6,016,049 | A | 1/2000 | Baughman et al. |
| 6,061,577 | A | 5/2000 | Andrieu et al. |
| 6,068,078 | A | 5/2000 | Rau et al. |
| 6,088,235 | A | 7/2000 | Chiao |
| 6,373,152 | B1 | 4/2002 | Wang et al. |
| 6,437,544 | B1 | 8/2002 | Yang |
| 6,534,965 | B2 | 3/2003 | Ueno et al. |
| 6,563,269 | B2 | 5/2003 | Robinett et al. |
| 6,566,853 | B2 | 5/2003 | Li et al. |
| 6,603,296 | B2 | 8/2003 | Conti et al. |
| 6,693,443 | B2 | 2/2004 | Ludwig et al. |
| 6,812,586 | B2 | 11/2004 | Wacknov et al. |
| 7,068,017 | B2 | 6/2006 | Willner et al. |
| 7,459,896 | B2 * | 12/2008 | Marcotte et al. ............ 324/71.4 |
| 8,928,306 | B2 * | 1/2015 | Marcotte et al. ............ 324/71.4 |
| 2002/0067143 | A1 | 6/2002 | Robinett et al. |
| 2002/0196956 | A1 | 12/2002 | Andersen et al. |
| 2005/0231185 | A1 | 10/2005 | Marcotte et al. |
| 2007/0017957 | A1 | 1/2007 | Tascone et al. |
| 2009/0058396 | A1 | 3/2009 | Marcotte et al. |

FOREIGN PATENT DOCUMENTS

| | | |
|---|---|---|
| CA | 2053298 A1 | 10/1990 |
| CA | 1315127 C | 3/1993 |
| CA | 1328679 C | 4/1994 |
| CA | 2558042 C | 4/2011 |
| EP | 1721128 A1 | 11/2006 |
| IN | 261893 | 7/2014 |
| JP | 2966475 B2 | 10/1999 |
| JP | 2000016321 A | 1/2000 |
| JP | 2004265320 A | 9/2004 |
| JP | 2007526459 A | 9/2007 |
| JP | 4653158 B9 | 12/2010 |
| KR | 20070017142 | 2/2007 |
| MX | 266494 | 5/2009 |

OTHER PUBLICATIONS

Barkhordarian, Vrej, "Power MOSFET Basics," http://www.irf.com/technical-info/appnotes/mosfet.pdf, International Rectifier, 13 pages.

U.S. Appl. No. 11/067,768, Non-Final Office Action mailed Mar. 21, 2007, 8 pages.

U.S. Appl. No. 11/067,768, Final Office Action mailed Sep. 14, 2007, 8 pages.

U.S. Appl. No. 11/067,768, Non-Final Office Action mailed Jan. 7, 2008, 9 pages.

U.S. Appl. No. 11/067,768, Notice of Allowance mailed Aug. 20, 2008, 5 Pages.

U.S. Appl. No. 12/290,257, Non-Final Office Action mailed Jun. 10, 2009, 7 pages.

U.S. Appl. No. 12/290,257, Final Office Action mailed Jan. 15, 2010, 9 Pages.

U.S. Appl. No. 12/290,257, Non-Final Office Action mailed May 17, 2010, 12 pages.

U.S. Appl. No. 12/290,257, Final Office Action mailed Dec. 28, 2010, 16 pages.

U.S. Appl. No. 12/290,257, Notice of Allowance mailed Aug. 8, 2014, 6 pages.

European Patent Application No. EP05714516.1, Supplementary Search Report mailed Mar. 6, 2014, 4 pages.

European Patent Application No. EP 05 714 516.1, Office Action mailed Apr. 29, 2015, 4 pages.

European Patent Application No. EP 15 15 7157.7, European Search Report mailed Jun. 9, 2015, 6 pages.

* cited by examiner

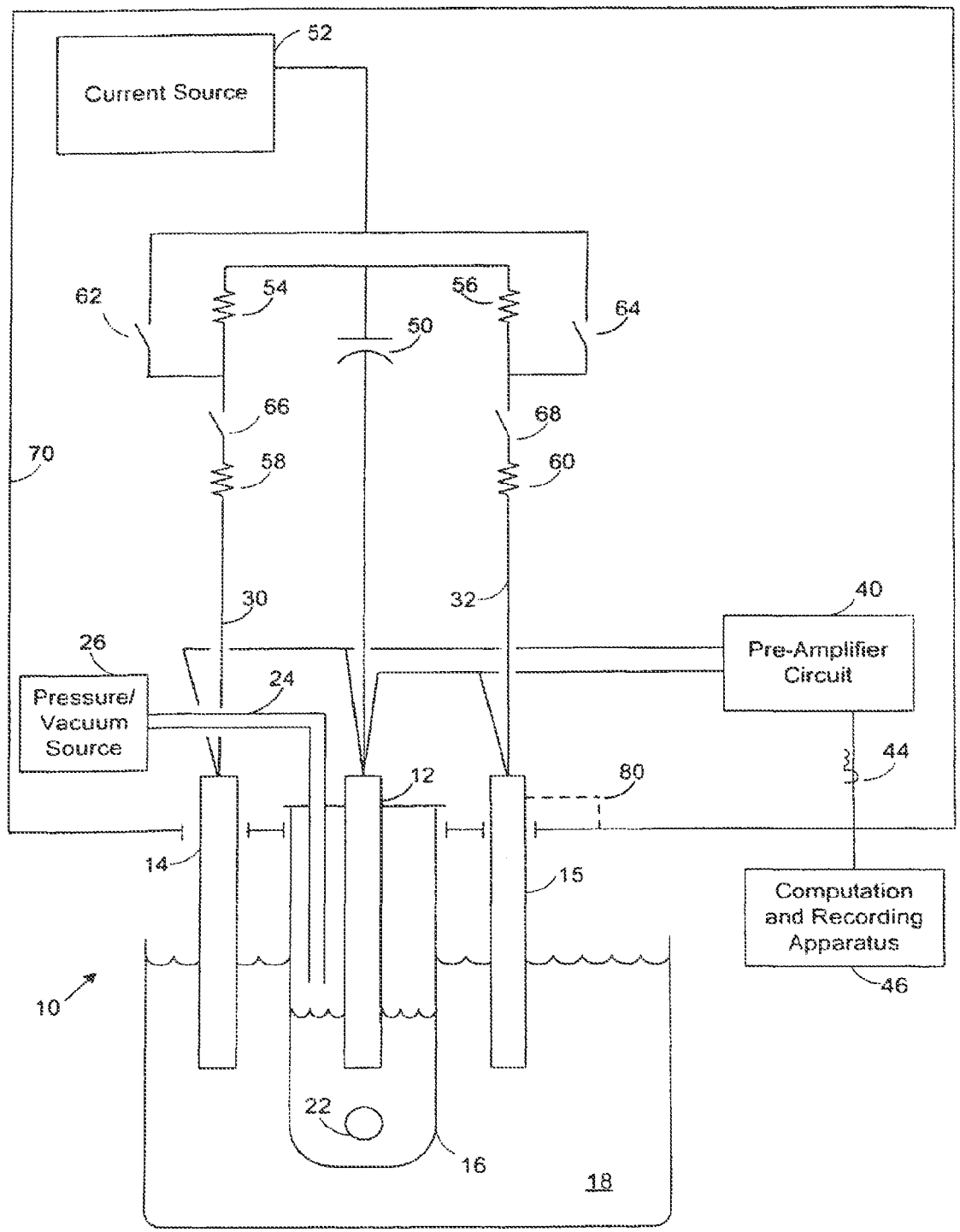

ELECTRODE CONFIGURATION FOR LIMCA

CROSS-REFERENCE TO RELATED APPLICATIONS

This application is a continuation of U.S. patent application Ser. No. 12/290,257 filed Oct. 29, 2008, which is a continuation of U.S. patent application Ser. No. 11/067,768 filed Feb. 28, 2005, issued as U.S. Pat. No. 7,459,896, which claims the priority right benefit of U.S. Provisional Patent Application No. 60/550,998 filed Mar. 4, 2004, the contents of each of which are incorporated in full by reference.

FIELD OF THE INVENTION

The invention generally relates to reducing electromagnetic noise pick up in an apparatus for detecting and measuring particles in molten metal.

BACKGROUND OF THE INVENTION

Molten metals, particularly molten aluminum and steel, are frequently contaminated by entrained non-metallic inclusions that give rise to a variety of shortcomings or defects in resulting products. These inclusions may cause the metal to tear during mechanical working operations, pin-holes and streaks in foils, surface defects and blisters in sheets, and increased rates of breakage during the production of wire.

One analyzer that provides quick results and includes size and concentration information of inclusions is a Liquid Metal Cleanliness Analyzers (LiMCA). An LiMCA may comprise an electrically insulating wall means, often in the form of a sampling tube, having a small, precisely-dimensioned passage in a side wall. The tube is immersed in the molten metal to be tested and a uniform stream thereof is passed through the passage while a substantially constant electric current is established through the stream between two electrodes disposed respectively inside and outside the tube. The particles of interest have very high resistivity compared to the molten metal and travel of a particle through the passage is accompanied by a change in resistance against the electric current producing an electrical pulse in the voltage. The number of pulses produced while a fixed volume of metal passes through the passage provides an indication of the number of particles per unit volume in the metal. Furthermore it is possible to analyze the pulse shape to determine particle size and size distribution.

The LiMCA apparatus has been designed for "on-line" tests, to give results in seconds, but this often means that the apparatus is close to the molten metal source and associated noise generating equipment.

Within the industrial environment of the LiMCA, there may be many sources of electrical or mechanical interference, or noise that affect the results of electrical pulse detection. It is difficult in practice to reliably extract the wanted pulse signals of the LiMCA system from these noise signals, since the noise may be of the same order of magnitude as the wanted pulse signals from detection of the smaller particles. To this end, it has traditionally been preferred that the supply current come from rechargeable batteries. Such batteries, for example Nickel-Cadmium types, can be recharged at points during the measurement cycle when data is not actually being collected but the use of batteries requires additional steps and equipment to ensure that charging is properly controlled. The batteries are also sensitive to high temperatures that can occur in the environment and are limited in the number of charge-discharge cycles that can be applied. A vacuum or pressure source is generally used to move the metal through the passage and should be free of pump-generated pulses that may interfere with the signal. The entire apparatus should also be shielded as much as possible against outside electromagnetic interference.

The design and use of filters to reduce or eliminate interference is now a well-developed art, but difficulties arise when used with LiMCA analyzers, due to the relatively low voltage signal characteristic of the particle-indicating pulses and the fact that the pulse frequencies, corresponding to the number of particles per unit time passing through the passage, are of the same order of magnitude as those of many of the interfering noise pulses. Shielding can be provided to reflect or absorb the broadcast radiation before it reaches the apparatus but it is impossible to achieve a perfect shielding because of the need for inputs and outputs to and from the system.

Typical LiMCA analyzers are described in U.S. Pat. Nos. 4,600,880, 5,130,639, 4,555,662 and 5,039,935, herein incorporated by reference. U.S. Pat. No. 5,130,639 (Hachey) describes the use of various combinations of electrodes in a LiMCA analyser where the measurement and current supply electrodes are separate and placed in noise reducing configurations. At least four, and up to six electrodes are required.

U.S. Patent Application No. 2002/0067143, also herein incorporated by reference, describes the use of ultra-capacitors as alternatives for batteries in certain applications. Ultra-capacitors can be used as power sources in harsh environments because they are less temperature sensitive than batteries and they can be rapidly charged and discharged compared to batteries, thereby requiring less control on the charging-discharging process, and have very large cycle life compared to batteries. However, ultra-capacitors have a lower volume charge density than rechargeable batteries and cannot therefore supply constant high currents for extended periods of time compared to batteries.

It is generally seen as desirable to develop an analyzer system that can reduce interference while simplifying design and requiring fewer additional parts.

It is further desirable to develop an analyzer system that can operate with increased continuity and overcome the deficiencies of battery operation.

SUMMARY OF THE INVENTION

The present invention provides a method of reducing electromagnetic noise in wanted pulse signals produced by a LiMCA analyzer, having a body of molten metal containing particles, electrically insulating wall means having a passage formed therein for passage of the molten metal, a first electrode inserted in the molten metal on one side of the wall means, a second and a third electrode inserted into the molten metal on an opposite side of the wall means to said first electrode and equally spaced on either side of the first electrode such that the three electrodes fall in a common plane, said method comprising steps of supplying current equally to the second and third electrodes, said current passing with the molten metal through the passage to the first electrode to create symmetrical current loops between each of the second and the third electrodes and the first electrode, which loops generate the wanted pulse signals and are affected in an equal but opposite manner by electromagnetic noise; and adding the wanted pulse signals generated by each current loop to at least reduce the electromagnetic noise.

The present invention further provides a method of making nearly continuous measurements in a LiMCA analyzer, having a body of molten metal containing particles, electrically insulating wall means having a passage formed therein for passage of the molten metal, a first electrode inserted in the molten metal on one side of the wall means and at least one additional electrode inserted in the molten metal on an opposite side of the wall means to the first electrode and voltage recording means connected between the first electrode and the at least one additional electrode, said method comprising supplying current at an initial predetermined level to the first electrode and to the at least one additional electrode to create a current loop between the at least one additional electrode and the first electrode, said current loop generating a wanted pulse signal that is recorded by the voltage recording means, wherein the said current is supplied from an ultra-capacitor, monitoring the change in the current from said ultra-capacitor and providing a means for rapidly re-adjusting the current output to the predetermined level while said voltage recording means is temporarily prevented from recording the wanted pulse signal.

The present invention also provides an apparatus for reducing electromagnetic noise in wanted pulse signals produced by a LiMCA analyzer, having a body of molten metal containing particles, electrically insulating wall means having a passage formed therein for passage of the molten metal and particles, an inside electrode inserted in the molten metal inside the wall means, and comprising a first and a second outside electrode inserted into the molten metal outside the wall means on either side of the inside electrode, to form a common plane with the inside electrode, a current source for supplying current equally to the first and the second outside electrodes, which current passes with the traveling molten metal through the passage to the inside electrode to create symmetrical current loops between each of the first and the second outside electrodes and the inside electrode that generate the wanted pulse signals, detection means connected to the first and the second outside electrodes and the inside electrode, for detecting wanted pulse signals generated by the current loops due to travel of particles through the passage, and for detecting electromagnetic noise that affects equally but in an opposite manner each of the current loops; and amplifier means for adding the wanted pulse signals generated by each current loop to at least reduce the electromagnetic noise.

BRIEF DESCRIPTION OF THE DRAWINGS

The present invention will be described in conjunction with the following FIGURE:

FIG. 1 is a schematic view of an embodiment of the present invention.

DETAILED DESCRIPTION OF PREFERRED EMBODIMENTS OF THE INVENTION

In the present invention, symmetrical and stable currents from electrodes on the outside of a passage in an electrically insulating wall to an electrode on the inside of the passage, together with simultaneous symmetrical voltage pick up, have been found to self-cancel external electromagnetic noise sources if these sources equally affect both current loops. For purposes of the present invention, a stable current is considered to be one that is relatively smooth and free of pulses.

FIG. 1 illustrates an LiMCA 10 according to an embodiment of the present invention. The LiMCA 10 comprises an insulating wall means in the form of a closed end sampling tube 16 immersed in molten metal 18 and sealed at its upper end to a mounting plate or tube (not shown), for example, by means of an elastomeric seal. Three transversely-spaced parallel electrodes 12, 14 and 15 extend downwardly into the molten metal with electrode 12 extending into the sampling tube 16 and electrodes 14 and 15 extending directly into the molten metal 18.

The tube 16 is provided with an accurately-formed borehole or passage 22 in a portion of its side wall. A line 24 disposed in the tube 16 is connected to a vacuum source 26 to establish a vacuum in a cell formed by the tube 16. Molten metal 18 is drawn into the cell through the passage 22 by the vacuum. Alternately, a pressure source 26 can be used to expel molten metal from the cell via the line 24.

Measurements are taken as follows. Once the cell is immersed in molten metal, a vacuum is applied and molten metal is drawn at a controlled rate through the passage 22. A stable current, usually of the order of 60-65 amps, is passed through the passage 22 by feeding equal currents (each being half the total current) to each of the electrodes 14 and 15, by way of current leads 30, 32. The current is returned via the single electrode 12 within the cell. The voltage is measured between each of the outer electrodes 14, 15 and the centre electrode 12 by means of a pre-amplifier 40 of a design known to those skilled in the art. The voltage changes as particles pass through the passage giving rise to voltage spikes. Once a predetermined amount of metal is drawn into the cell, sufficient to allow enough voltage spike measurements to be taken to provide statistically meaningful results, the measurements are halted, pressure is applied to eject the metal, and the process may be repeated.

The number of voltage spikes measured is used to determine the volume density of particles in the molten metal and the pulse shape may be analysed to determine particle size distributions. The measurement period should be long enough to provide a sufficient sample size of voltage pulse measurements for a statistically meaningful measurement, and to increase the overall signal to noise ratio.

Whilst the current may be supplied by a battery arrangement, for example, as described in U.S. Pat. No. 5,130,639, it is preferred that the current be supplied by a supply system which consists of an ultra-capacitor 50 a current source 52 fixed shunt resistors 54,56, and voltage controlled resistors 58,60. In use, the ultra-capacitor 50 is initially charged or recharged while measurements are not being taken, by closing switches 62, 64. Charging is carried out to a predetermined level, determined by the charging supply and capacitor specifications and is typically 11000 Coulombs (amp-seconds). This charging/recharging can occur, for example, during the period of time that a sample of metal is being expelled from the cell. Once charged, the switches 62, 64 are opened. During the measurement period, discharge switches 66, 68 are closed, and a current, controlled by the voltage on the capacitor 50 and the value of the shunt and voltage controlled resistors 54, 56, 58 and 60 (and measured, for example, by the voltage drop across the shunt resistors 54, 56) flows through the outer electrodes 14, 15, through the passage and returns via the central electrode 12. The voltage controlled resistances are preset so that the current initially flows at predetermined value, for example, 32.5 amps equally through each of the pair of resistances. During measurements, the current tends to decay. Because the volume charge density of the ultra-capacitor 50 is relatively low compared to a battery, the decay is sufficiently fast that the current would fall to an unacceptable level before the measurement is complete. A too-low current would lead to the voltage pulse height becoming too low to provide a clear differentiation from background noise. To overcome this problem, when the current (as measured for example by the voltage drop across the shunt resistors 54, 56) falls below a predetermined level, for example about 90% of the initial current, the measurements are suspended and the voltage controlled resistors 58, 60 are adjusted to return the current to the initial value. This process may be repeated several times during the course of one measurement, wherein a measurement is defined as the time to draw the metal sample into the cell. The ultra-capacitor 50 itself is conveniently and rapidly recharged to its full charge during the step of expelling metal from the cell, during which time, measurements are not taken. It should be noted that a current source based on an ultra-capacitor 50 and as described as above may also be effectively used with other types of LiMCA apparatus, for example as described in U.S. Pat. Nos. 4,600,880, 5,130,639, 4,555,662 and 5,039,935, where a comparable current is required for measurements and the metal is drawn into and expelled from a similar cell.

Common sources of interference for the LiMCA 10 are induction furnaces, which broadcast punctual and continuous bursts of strong interference that are easily confused with the wanted pulse signals, thus filters, shields and insulation have limited efficiency. LiMCA analyzers are also often used directly in molten metal processing facilities and are located in close proximity to the induction furnace, well within the broadcast area of the interference signal. The bursts of interference produced by the induction furnace and also any mechanical vibrations are picked up by the electrodes 12, 14, 15 in the form of interference, or noise. While a signal pre-amplifier can amplify the wanted pulse signals for better reading, it cannot be located to receive the wanted signals without also receiving the interference.

All three electrodes 12, 14 and 15 may lie in the same plane. The electrodes 14 and 15 are disposed on the opposite side of the electrode 12 and are equally spaced from the electrode 12 so that the electrodes 14 and 15 interact in a similar manner with the externally generated interference to thereby cancel out the interference signal. The current flowing through the outer electrodes 14 and 15 induces magnetic fields in each of the current loops. These magnetic fields are balanced, thereby minimizing the combined, detected effect of noise, generally caused by vibrations, that is picked up by outside electrodes 14 and 15, which are equally exposed to magnetic fields. Also, balanced magnetic fields minimize noise generation by the instrument itself resulting from electrical transients that arise when the measurement current is turned on or off.

The signal, containing the wanted pulse signal detected between the electrode 12 and the electrodes 14 and 15 is fed to detection means such as a differential preamplifier circuit 40 to amplify the wanted pulse signals while rejecting the equal and opposite electromagnetic noise signals. From the differential preamplifier circuit 40 the signal is then fed for further analysis and display to a computation and recording apparatus 46. To further protect against noise, the preamplifier 40 and computing and recording apparatus 46 may be decoupled, for example by opto-couplers 44. The pre-amplifier 40 as well can be operated from a rechargeable battery or more preferable from an ultra-capacitor (not shown), which can be recharged periodically from a disconnectable power supply (also not shown).

An exemplary embodiment of such a computing and recording apparatus 46 can be seen in U.S. Pat. Nos. 4,555,662 and 4,600,880 incorporated herein by reference. The recording apparatus 46 takes the pulse signals resulting from the travel of particles through the passage 22 in the insulating wall 16 and produces a permanent visible record indicating the number of particles per unit volume of molten metal 18, their individual size if required, and their relative size distribution.

All critical electronics are preferably placed within a shielding enclosure 70 to shield the electronics themselves from picking up noise. The shielding enclosure 70 can be connected as shown by the dotted connection 80 to one of the two electrodes 14 or 15 to establish the molten metal as reference. Alternatively, for further noise reduction, the enclosure 70 may be connected to a separate (fourth) electrode, not shown, immersed in the molten metal in which case the connection 80 is removed.

The electrode structures disclosed enable the LiMCA device to detect relatively small size particles and, as discussed above, minimize noise and interference to enable the relatively small, wanted signals to be adequately identified.

In the above embodiments of the invention, the molten metal may be any molten metal, such as a flowing stream passing in a transfer trough.

Although in the above embodiments analyzing is carried out while a vacuum 26 draws the molten metal 18 into the tube 16, it is also possible to test while the metal 18 is expelled from the tube 16 by an internally applied pressure in which case the recharging of the ultra-capacitor 50 would be carried out during the period the metal was drawn into the cell.

This detailed description of the apparatus is used to illustrate the prime embodiment of the system and the method of the present invention. It will be obvious to those skilled in the art that various modifications can be made in the present apparatus of the system and that various alternative embodiments can be utilized. Therefore, it will be recognized that various modifications can be made in both the method and apparatus of the present invention and in the applications to which the method and system are applied without departing from the scope of the invention, which is limited only by the appended claims.

What is claimed is:

1. An apparatus for making measurements in a Liquid Metal Cleanliness Analyzer (LiMCA), having a body of molten metal containing particles, an electrically insulating unit having a passage formed therein for passage of the molten metal, the apparatus comprising:
   a first electrode positioned on one side of the electrically insulating unit;
   at least one additional electrode inserted in the molten metal on an opposite side of the electrically insulating unit to the first electrode;
   at least one voltage control resistor associated with the at least one additional electrode;
   a voltage recording device connected between the first electrode and the at least one additional electrode; and
   a current source configured to supply current at an initial predetermined level to the first electrode and to the at least one additional electrode to create a current loop between the at least one additional electrode and the first electrode, the current loop generating a wanted pulse signal that is recorded by the voltage recording device,
   wherein the apparatus is configured to adjust the at least one voltage control resistor associated with the at least one additional electrode to re-adjust the current output to the predetermined level during the course of one measurement while the voltage recording device is temporarily prevented from recording the wanted pulse signal, thereby maintaining the supply of current at the predetermined level for a period of time required for the one measurement.

2. The apparatus of claim 1, wherein the current is supplied from an ultra-capacitor via the at least one voltage control resistor associated with the at least one additional electrode.

3. The apparatus of claim 2, wherein the ultra-capacitor recharges between measurements.

4. The apparatus of claim 1, wherein the electrically insulating unit comprises a closed end sampling tube and the one measurement occurs while molten metal flows through the passage into the closed end sampling tube.

5. The apparatus of claim 4, further comprising a vacuum source for drawing the molten metal into the closed end sampling tube.

6. The apparatus of claim 1, wherein the electrically insulating unit comprises a closed end sampling tube and the one measurement occurs while molten metal flows through the passage out of the closed end sampling tube.

7. The apparatus of claim 6, further comprising a pressure source for expelling the molten metal out of the closed end sampling tube.

8. The apparatus of claim 1, wherein the first electrode and the at least one additional electrode are coplanar.

9. The apparatus of claim 1, further comprising a reference electrode that is inserted into the molten metal and connected to an enclosure surrounding at least the current source to establish the molten metal as a voltage reference point.

10. The apparatus of claim 1, further comprising a circuit for adding the wanted pulse signals generated by each current loop to at least reduce electromagnetic noise.

11. A method of making measurements in a Liquid Metal Cleanliness Analyzer (LiMCA), having a body of molten metal containing particles, an electrically insulating unit having a passage formed therein for passage of the molten metal, a first electrode positioned on one side of the electrically insulating unit and at least one additional electrode inserted in the molten metal on an opposite side of the electrically insulating unit to the first electrode and a voltage recording device connected between the first electrode and the at least one additional electrode, the method comprising:

supplying current at an initial predetermined level to the first electrode and to the at least one additional electrode to create a current loop between the at least one additional electrode and the first electrode, the current loop generating a wanted pulse signal that is recorded by the voltage recording device;

monitoring the change in the current; and adjusting the at least one voltage control resistor associated with the at least one additional electrode to re-adjust the current output to the predetermined level during the course of one measurement while the voltage recording device is temporarily prevented from recording the wanted pulse signal, thereby maintaining the supply of current at the predetermined level for a period of time required for the one measurement.

12. The method of claim 11, wherein the current is supplied from an ultra-capacitor via the at least one voltage control resistor associated with the at least one additional electrode.

13. The method of claim 12, further comprising recharging the ultra-capacitor between measurements.

14. The method of claim 11, wherein the electrically insulating unit comprises a closed end sampling tube, the method further comprising drawing the molten metal through the passage into the closed end sampling tube during the one measurement.

15. The method of claim 14, further comprising using a vacuum source to draw the molten metal into the closed end sampling tube.

16. The method of claim 11, wherein the electrically insulating unit comprises a closed end sampling tube, the method further comprising expelling the molten metal through the passage out of the closed end sampling tube during the one measurement.

17. The method of claim 16, further comprising using a pressure source to expel the molten metal out of the closed end sampling tube.

18. The method of claim 11, further comprising arranging the first electrode and the at least one additional electrode so they are coplanar.

19. The method of claim 11, further comprising establishing the molten metal as a voltage reference point by inserting a reference electrode into the molten metal and connecting the reference electrode to an enclosure surrounding at least the current source.

20. The method of claim 11, further comprising reducing electromagnetic noise by adding the wanted pulse signals generated by each current loop.

* * * * *